United States Patent [19]

Zeldin et al.

[11] Patent Number: 4,997,944

[45] Date of Patent: Mar. 5, 1991

[54] AMINOPYRIDYL SILANES

[75] Inventors: Martel Zeldin; Wilmer K. Fife, both of Indianapolis, Ind.

[73] Assignee: Indiana University Foundation, Bloomington, Ind.

[21] Appl. No.: 467,053

[22] Filed: Jan. 18, 1990

[51] Int. Cl.$^5$ ............................................. C09F 7/10
[52] U.S. Cl. ...................................................... 546/14
[58] Field of Search ......................................... 546/14

[56] References Cited

U.S. PATENT DOCUMENTS

| 2,854,455 | 9/1958 | Cislak | 546/14 |
| 4,855,433 | 8/1989 | Zeldin | 546/14 |
| 4,864,027 | 9/1989 | Shubert et al. | 546/14 |

OTHER PUBLICATIONS

Frechet et al., "Reactive Polymers: Design Considerations, Novel Preparations and Selected Applications in Organic Chemistry" *Pure Appl. Chem.*, 1988, 60, 353.
Menger et al., "A Polymer-Bound 4-Aminopyridine; Synthesis and Reactivity," J. Org. Chem., 1985, p. 3928.
Mathias et al., "Synthesis, Chclopolymerization, and Cyclocopolymerization of 4-(Diallylamino)Pyridine: A New Monomer" *J. Polym. Lett. Ed.* 1985, 23, 147.
Mathias et al., "Inverse Phase Transfer Catalysis, First Report of a New Class of Interfacial Reactions" *J. Am. Chem. Soc.* 1986, 108, 1093-1094.
Vaidya et al., "Polymeric Supernucleophilic Pyridine Catalysts: Homogeneous Esterolysis of p-Nitrophenyl Esters" *J. Am. Chem. Soc.* 1986, 108, 5514-5520.

*Primary Examiner*—Richard L. Raymond
*Assistant Examiner*—Raymond Covington
*Attorney, Agent, or Firm*—Woodward, Emhardt, Naughton, Moriarty & McNett

[57] ABSTRACT

Silanes and siloxanes incorporating the 4-dialkylaminopyridine functionality are described. Preferred silanes are catalytically active and also serve as precursors to the siloxanes. Preferred siloxanes incorporating DAAP functionality exhibit excellent physical and dynamic-mechanical properties while maintaining a substantial percentage of the DAAP catalytic behavior.

21 Claims, No Drawings

AMINOPYRIDYL SILANES

BACKGROUND OF THE INVENTION

This invention resides generally in the fields of pyridine, silicon and catalyst chemistry. More particularly, it relates to heat-stable nucleophilic compositions comprising siloxanes containing 4-dialkylaminopyridine functional groups, and to their silane precursors, both of which are highly effective as catalysts in numerous organic reactions.

By way of further background, 4-dialkylaminopyridines ("DAAP's") are highly nucleophilic and exhibit catalytic activity toward a variety of reactions including acylations of derivatives of carbon, phosphorous and sulfur acids, and in silylations, ester rearrangements, polymerizations, redox and other reactions. Early catalytic work with such DAAP compounds involved monomolecular species including, for instance, extensive work both commercially and in the literature with 4-dimethylaminopyridine (commonly referred to as "DMAP"). DMAP itself exhibits remarkable catalytic activity and has become a standard by which the activity of other DAAP compounds is often measured. For example, the efficacy of a subject DAAP compound in catalyzing a transacylation reaction of a sterically hindered alcohol such as 1-methylcyclohexanol with an anhydride such as acetic anhydride is commonly compared to that of DMAP. In such comparisons, the rate of the transacylation catalyzed by DMAP may be assigned a relative value of 1 (i.e., 100%), and the relative catalytic rate of the other DAAP compound is expressed as a fraction (i.e. percentage) thereof.

More recent work in this field has involved attempts to incorporate DAAP functionality into polymers while maintaining as much of its catalytic activity as possible. In so doing, the hope is that polymeric catalyst compositions may be formed which exhibit a wide range of valuable chemical, physical and dynamic-mechanical properties which prove more adaptable to varied uses than their monomeric counterparts.

For example, several vinyl-based polymeric catalysts with pendant DAAP groups have been prepared, including for instance: (1) poly[N-methyl-N-(4-vinylbenzyl)aminopyridine], Menger, F. M., McCann, D. J., J. Org. Chem. 1985, 50, 3928; (2) poly(diallylaminopyridine), Mathias, L. J., Vaidya, R. A., Bloodworth, R. H., J. Polym. Lett. Ed. 1985, 23, 147; Mathias, L. J., Vaidya, R. A., J. Am. Chem. Soc. 1986, 108, 1093; and Vaidya, R. A., Mathias, L. J., ibid 1986, 108, 5514; and (3) poly[methyl(3-styrenylpropyl)aminopyridine] cross-linked with divinylbenzene, Frechet, J. M. J., Darling, G. D., Itsuno, S., Lu, P., de Meftahi, M. N., Rolls Jr., W. A., Pure Appl. Chem. 1988 60. 353. However these vinyl-based catalyst materials have generally suffered in that they thermally degrade at temperatures below 300° C. and thus cannot effectively be used at higher temperatures which are preferred for many reactions. Further, in many instances the polymer-supported DAAP functions have been appended to their vinyl backbones in ways that significantly decrease their catalytic activities.

These and other considerations have represented significant drawbacks to this point in the development of truly satisfactory polymeric catalyst materials not only having effective DAAP functionality, but also exhibiting physical, chemical and dynamic-mechanical properties which make them applicable over a wide range of reactions and reaction conditions. Consequently, the need for such polymeric catalysts has continued for some time.

SUMMARY OF THE INVENTION

The applicants' invention addresses this need by providing novel compositions comprising silane monomers and siloxane polymers incorporating effective dialkylaminopyridine functionalities. The preferred silanes are catalytically active whether in solution or bound to suitable substrates, and also serve as precursors to the siloxane polymers. These silanes comprise at least one 4-dialkylaminopyridine functional group having at least one functionalized (e.g. alkoxy-) silyl component connected to its 4-dialkylamino moiety. Also, the preferred silanes are in one embodiment at least di-functional for use as precursor materials for siloxane polymers. As examples, this difunctionalization can be achieved by the presence of one dialkoxysilyl group or two monoalkoxysilyl groups.

The preferred siloxanes have DAAP groups pendant from or included within their polymer backbones, and exhibit heat stabilities far superior to their heretofore-known vinyl-based counterparts. These siloxanes can be linear or cross-linked and homo- or copolymers, and are formed as fluids, gums, gels, elastomers or resinous materials, depending upon various factors including their degree of cross-linking, if any. As to their efficacy, for example, these siloxanes have catalyzed the transacylation of 1-methylcyclohexanol and acetic anhydride at rates approaching about 75% and above that of monomolecular DMAP, with rates of about 80%-90% or greater being experienced in several instances. In addition, these siloxane materials have preserved their catalytic activity over a wide temperature range from about −100° C. to 375° C. and above.

Accordingly, one object of the invention is to provide methods for preparing and compositions comprising novel silanes and siloxanes having DAAP functionalities.

Another object of the invention is to provide siloxane polymers with DAAP groups pendant from or incorporated in their polymer backbones which possess high chemical activity and thermal stability, and preserve physical and dynamic-mechanical properties over a wide temperature range.

Another object of the invention is to provide compositions comprising silanes having DAAP functionalities which are themselves useful as catalysts, anti-corrosive agents and anti-oxidants, and al$o as precursors to their corresponding siloxane polymers.

Another object of the invention is to provide novel methods for preparing aminopyridyl silanes and siloxanes.

Other objects and advantages of the invention will be apparent from reading the description which follows.

DESCRIPTION OF THE PREFERRED EMBODIMENT

For the purposes of promoting an understanding of the principles of the invention, reference will now be made to various preferred embodiments and specific language will be used to describe the same. It will nevertheless be understood that no limitation of the scope of the invention is thereby intended, and that such alterations and further modifications and applications of the principles of the preferred embodiments as described herein as would normally occur to one skilled in the art to which the invention relates are contemplated as falling within the spirit and scope of the invention.

In accordance with the discussion above, one preferred embodiment of the invention relates to a composition comprising a silane or siloxane incorporating significant 4-dialkylaminopyridine functionality. The preferred materials exhibit strong nucleophilic and basic properties, and have utility in a wide variety of catalytic, acid scavenging, metal ion-sequestering and other applications well within the purview of those ordinarily skilled in these areas. In addition, the preferred siloxane polymers have demonstrated remarkable thermal stability up to 375° C. and above while preserving desirable catalytic and dynamic-mechanical properties over a wide temperature range from about −100° C. to 375° C. and above. The preferred siloxanes are thus good materials for general DAAP-type catalytic applications, far superior to their vinyl-based counterparts to date which suffer in many respects as noted above.

The preferred silanes comprise a (i.e. at least one) 4-dialkylaminopyridine function having at least one silyl component attached to its 4-dialkylamino moiety. This silyl component is in turn functionalized with one, two or three radicals which facilitate the polymerization and/or substrate binding process. To date, the applicants have worked with alkoxy groups in this position. However, the significance of these alkoxy or other radicals is that they functionalize the silyl component by providing a silicon bond which is labile in aqueous or other protic solvents. As is well known and understood by those skilled in this area, there are many other groups which possess this same functionalizing property and are effective substitutes for the alkoxy groups in the applicants' experiments so far. For instance, these include cycloalkoxy (e.g., -O-cylcohexyl), aralkoxy and acyloxy groups, amino groups, halo groups (preferably chloro), and many others.

In other preferred embodiments these silanes have two such silyl components connected to the DAAP function, and are preferably at least difunctional to enable their expedient polymerization to corresponding siloxanes as discussed below. This latter embodiment is achieved, for example, where the silane incorporates either a single dialkoxysilyl group or two monoalkoxysilyl groups in its structure.

Accordingly, it is possible to depict particularly preferred silanes of 1 he invention in the following formulas:

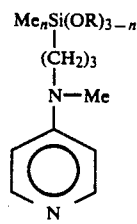

and

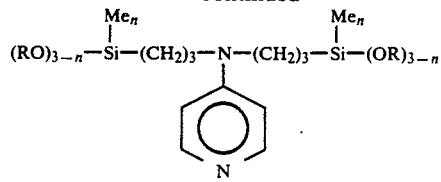

wherein n=0, 1 or 2 and R to date comprises lower alkyls with methyl, ethyl, propyl and iso-propyl being preferred thus far. As those skilled in this field will appreciate, however, these only represent and define representative examples while other suitable silanes within the spirit and scope of the invention can be readily prepared with similar effective properties and being at least functional equivalents to those defined above. For instance, the spacer group separating the aminopyridyl moiety from the silicon, i.e. trimethylene $[(CH_2)_3]$ in the formulas above, can be another organic group, including for instance a shorter or longer, branched or unbranched radical that may be an alkyl, aryl or aralkyl (i.e. benzyl) group. Such replacements are well within the knowledge and skill of those experienced in this field in view of a specific circumstance or compound under consideration.

Similarly, the methyl groups defined above can likewise be replaced with other organic groups. These include longer, branched or unbranched alkyl groups such as ethyl, propyl, iso-propyl, butyl, iso-butyl, etc., as well as aryl or aralkyl and other groups, all of which have effective properties to function within the invention as defined and claimed herein.

With the foregoing in mind, the preferred silanes identified to date according to the above formulas are as follows:

No. Name
1a. N-(3-(Diethoxy(methyl)silyl)propyl)-N-methyl-4-aminopyridine
1b. N-(3-(Triethoxysilyl)propyl)-N-methyl-4-aminopyridine
2a. N,N[Bis(3-(dimethyl(ethoxy)silyl)propyl)]-4-aminopyridine
2b. N,N[Bis(3-(diethoxy(methyl)silyl)propyl)]-4-aminopyridine
2c. N,N[Bis(3-(triethoxysilyl)propyl)]-4-aminopyridine To date, the preferred process used to prepare these silanes has comprised the step of hydrosilating a 4-allylmethylamino- or a 4-diallylaminopyridine with an alkoxyhydrosilane (e.g. $Me_nSiH(OR)_{3-n}$ where n=0, 1 or 2 and R=methyl, ethyl, propyl, iso-propyl, etc.). For example, preferred silanes have been prepared by hydrosilation of 4-(N-methylallylamino)pyridine or 4-(N-diallylamino)pyridine with triethoxysilane [(EtO)₃SiH], diethoxy(methyl)silane [(EtO)₂MeSiH] or dimethyl(ethoxy)silane [(EtO)Me₂SiH]. These hydrosilations have taken place upon heating the reactants in the presence of a suitable catalyst such as chloroplatinic acid or a coordination complex such as PdCl₂, RhCl(PPh₃)₃ or Co(CO)₈. Specific parameters such as catalyst and solvent selection, and reaction temperatures, pressures, and duration are often interdependent and will vary according to the specific chemistry involved. In any event, the selection and optimization of these and other parameters are well within the skills of those practiced in this area. As to preferred process conditions thus far, the applicants have conducted their hydrosilations under vacuum at temperatures and for times of about 130° C. and 10 hours, respectively. The preferred silanes have thereby been formed as colorless liquids and can be characterized by one or more of elemental analysis, infrared-, $^1$H- and $^{13}$C-NMR spectroscopy, and gas chromatography-mass spectrometry.

In accordance with the discussion above, another preferred aspect of the invention relates to siloxane polymers incorporating these same significant DAAP functionalities. In this regard, the term "siloxane" is known in the art and used herein to mean a polymer containing repeating —Si—O— units in its backbone. Such —Si—O— units have occurred with or without other intermittent backbone structures. Certain preferred siloxanes of the invention exemplify the former type of backbone structure, and accordingly have had backbones with repeating units of —Si—O—Si—R—Si—O— wherein R is a nitrogenous organic component (e.g. siloxane species 5a, 5b, 6a and 6b identified below) which includes the DAAP function. Other preferred siloxanes have exemplified the latter type (e.g. species 3a, 3b, 4a and 4b below).

The preferred siloxanes incorporating these DAAP functionalities prepared to date have exhibited remarkable physical and dynamic-mechanical properties as evidenced in the specific Examples below. For example, they have demonstrated excellent heat stability, having degradation temperatures ("$T_d$'s") generally in excess of about 375° C. and in some instances of about 450° C. and even greater dependent upon such factors as molecular weights, degree of crosslinking, the particular reactants and their amounts, and to some extent upon the purity achieved. This thermal stability far surpasses that of their prior art vinyl-based counterparts which generally degrade at temperatures below 300° C., and enables their effective use in more and diverse reactions and reaction conditions. Also, the DAAP functions present have been incorporated into these preferred siloxanes while maintaining a substantial percentage of their original catalytic activities. This is evidenced, for example, in the experimental results presented in Example 13 and Table 2 below, in which preferred siloxanes of this invention have proven to generally catalyze the transacylation of 1-methylcyclohexanol and acetic anhydride at rates of about 75% or above that of conventional monomeric DMAP, with rates of about 80%–90% or above being experienced in some instances.

As to structure and attendant physical properties, the applicants' preferred siloxanes have been prepared as homo- or copolymers, linear or cross-linked, and in some instances have been end-blocked as further discussed below. These siloxanes are formed as fluids, gums, swellable gels, elastomers or resinous materials, largely depending upon the degree of their cross-linking, if any, as well their molecular weight (degree of polymerization) and other factors well known to those experienced in this area. In addition, preferred linear siloxane homo- and copolymers prepared according to the invention have been soluble in organic solvents, and have exhibited variation in molecular weights ranging from about $3 \times 10^3$ to about $1 \times 10^6$. More particularly, homopolymers thus far prepared have generally shown molecular weights less than about $1 \times 10^4$ while copolymers have shown molecular weights up to about $1 \times 10^6$.

As discussed above, the DAAP functionality in these preferred polymers has been pendant from or incorporated into the siloxane polymer backbones. As examples, preferred linear (i.e., 3a and 3b) and crosslinked (i.e., 4a and 4b) polymers having pendant DAAP groups have been prepared having repeating units consistent with the following formulas:

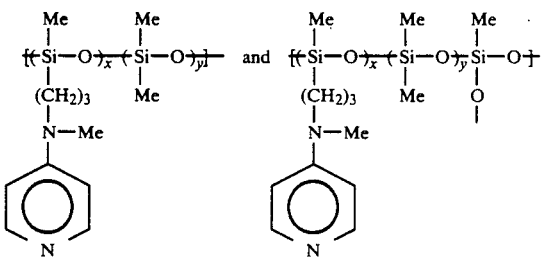

3a. x > 0, y = 0  
3b. x > 0, y > 0

4a. x > 0, y = 0  
4b. x > 0, y > 0

Preferred linear (i.e., 5a and 5b) and crosslinked (i.e., 6a and 6b) siloxane polymers having DAAP groups included within the polymer backbones have been prepared having repeating units consistent with the following formulas:

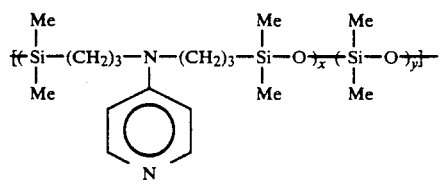

5a. x > 0, y = 0  
5b. x > 0, y > 0 and

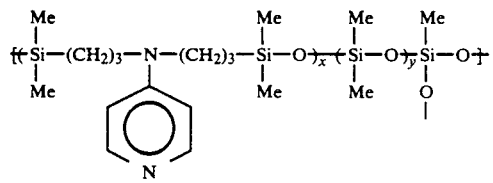

6a. x > 0, y = 0  
6b. x > 0, y > 0

As to their preparation, these preferred siloxane materials have been prepared to date by hydrolysis polymerization of a suitable silane monomer as described in detail above which includes a 4-dialkylaminopyridine function having an alkoxysilyl group attached to its 4-dialkylamino moiety. These polymerizations have occurred in the presence of a suitable base catalyst therefor as those practiced in this field will recognize. For instance, suitable catalysts for this operation generally include, but are not limited to, negatively-charged oxygen species such as hydroxide ion, which can be provided by suitable salts such as Me$_4$NOH, KOH and many others also known in the art.

As specific examples, linear siloxane homopolymers such as those of 3a and 5a above have been prepared by base-catalyzed hydrolytic polycondensations of difunctional silane monomers such as 1a and 2a above in THF/H$_2$O mixtures. Resulting hydroxyl-terminated siloxanes may be end-blocked with a suitable end-blocking agent such as (Me$_3$Si)$_2$O, (Me$_3$Si)$_2$NH, Me$_3$SiX (where X is a halogen such as Cl, or alkoxy such as methoxy, ethoxy, or propoxy), or bis(trimethylsilyl- )acetamide. The molecular weight ($M_n$) of the polymer obtained has depended upon factors such as the monomer:catalyst ratio used, and has been determined in the Examples below using exclusion chromatography and viscosity measurements. The preferred fluid polymers of the invention are soluble in chlorinated hydrocarbons, THF and alcohols.

Copolymers such as 3b and 5b above incorporating —Me$_2$SiO— units into their polymer backbones have also been prepared by reaction of difunctional silane monomers such as 1a and 2a above either with Me$_2$Si(OEt)$_2$ by hydrolytic polycondensation or with linear or cyclic siloxane oligomers (e.g. HO(SiMe$_2$O)$_x$H, (Me$_2$SiO)$_3$ or (Me$_2$SiO)$_4$) by ring opening redistribution polymerization. As is known in the art, other linear or cyclic siloxane oligomers can be used effectively in such copolymerization procedures, where instead of the methyl groups they include other organic radicals such as longer alkyl chains (e.g. ethyl, propyl, butyl, etc), cycloalkyl, aryl or aralkyl groups. These are accordingly contemplated within the scope of the invention as described and claimed herein. Each such copolymerization method leads to high molecular weight materials, generally $M_n > 1 \times 10^5$, with the specific comPosition being determined by the relative quantities of reactants, the presence and amount of end-blocking agents (e.g., (Me$_3$Si)$_2$O), and other factors.

A variety of crosslinked materials as represented by 4a, 4b, 6a and 6b above have also been prepared. Some of these preferred crosslinked siloxanes have been obtained by polymerization of difunctionalized DAAP-containing silanes such as those of 1a and 2a above in the presence of tri- or tetrafunctional silanes such as Me$_n$Si(OEt)$_{4-n}$ where n is 0 or 1, respectively. Others have been prepared by polymerization of at least trifunctional DAAP-containing silanes, for example those of 2b and 2c above, with possible inclusion of cyclic or linear dimethylsiloxyl oligomers and in the presence of these same tri- or tetrafunctional silanes. These crosslinked polymers and co-polymers have to date formed swellable gels, elastomers or insoluble resins depending upon their degrees of crosslinking and other factors. Further details as to preferred siloxanes can be found in Examples 6-12 below.

As also indicated above, one accepted standard way to test the ability of a catalyst to effect a reaction such as a transacylation is to evaluate its efficacy in catalyzing the reaction of a sterically hindered alcohol such as 1-methylcyclohexanol with an anhydride such as acetic anhydride. Thus, as is detailed in Example 13 and accompanying Table 2 below, several known and new DAAP materials were compared as to their rates of catalysis of this 1-methylcyclohexanol/acetic anhydride transacylation. As Table 2 evidences, the preferred siloxanes of this invention compare very favorably to the listed vinyl-based polymers with pendant DAAP functions, and consistently catalyzed this transacylation reaction at rates greater than about 75% that of DMAP, and in some instances were tested at about 80%-90% or above that of DMAP.

EXAMPLE 1

Synthesis of Silane Monomer 1a:
N-(3-(Diethoxy(methyl)silyl)propyl)-N-methyl-4-aminopyridine Silane 1a was prepared by first preparing and then hydrosilating 4-(N-methylallylamino)pyridine with diethoxy(methyl)silane, (EtO)$_2$MeSiH. The 4-(N-methylallylamino)pyridine was first obtained by reaction of 4-chloropyridine and N-methylallylamine. Thus, 4-chloropyridine (11.4 g; 0.1 mol) and N-methylallylamine (7.1 g; 0.1 mol) were combined in a glass ampoule or steel container, after which the mixture was degassed under vacuum and the vessel was sealed. The vessel was heated for three days at 130° C. The vessel was thereafter opened and the contents were dissolved in water and then neutralized with 10% aqueous NaOH. The aqueous solution was extracted with several portions of diethyl ether. The ether extract was filtered and evaporated. The residue was distilled under vacuum to give 4-(N-methylallylamino)pyridine (11.1 g; 75%; b.p. 70° C. @ 0.1 torr). 4-(N-Methylallylamino)pyridine (4.45 g; 0.030 mol), MeSiH(OR)$_2$(6.7 g; 0.050 mol) and H$_2$PtCl$_6$(60 µL; 0.080 mol/L in i-PrOH; 4.6×10$^{-6}$ mol) were combined and heated under vacuum in a sealed vessel for 10 hours at 130° C. Distillation of the products gave Silane 1a, N-(3-(diethoxy(methyl)silyl)propyl)-N-methyl-4-aminopyridine, as a colorless liquid (6.3 g; 74%; b.p. 122°-127° C. @ 0.05 torr). The product was characterized by elemental analysis infrared, $^1$H and $^{13}$C-NMR spectroscopy, and gas chromatography-mass spectrometry.

EXAMPLE 2

Synthesis of Silane Monomer 1b:
N-(3-(Triethoxysilyl)propyl)-N-methyl-4-aminopyridine To prepare silane 1b, the procedure of Example 1 was repeated except triethoxysilane [(EtO)$_3$SiH] was used instead of the diethoxy(methyl)silane. Silane 1b, N-(3-(triethoxysilyl)Propyl)-N-methyl-4-aminopyridine, was formed as a colorless liquid (40% yield, b.p. 135°-140° C. @ 0.05 torr) and was characterized by elemental analysis, infrared, $^1$H and $^{13}$C-NMR spectroscopy, and gas chromatography-mass spectrometry.

EXAMPLE 3

Synthesis of Silane Monomer 2a:
N,N[bis(3-(dimethyl(ethoxy)silyl)propyl)]-4-aminopyridine The title compound was prepared by hydrosilation of 4-diallylaminopyridine with dimethyl(ethoxy)silane, (EtO)Me$_2$SiH. The 4-diallylaminopyridine was obtained by reaction of 4-chloropyridine with diallylamine. Thus, in an experiment similar to that described in Example 1, 4-chloropyridine (11.2 g; 0.10 mol) and diallylamine (14.6 g; 0.15 mol) were combined in an ampoule, degassed under vacuum, sealed and heated for three days at 130° C. The product mixture was dissolved in water, neutralized with 10% NaOH and extracted with several portions of diethyl ether. The ether solution was filtered, the solvent was evaporated, and the residue was distilled to give 4-diallylaminopyridine (11.3 g; 65%; b.p. 92° C.@ 0.25 torr). 4-Diallylaminopyridine (5.2 g; 0.030 mol), (EtO)Me$_2$SiH (8.3g; 0.080 mol), and H$_2$PtCl$_6$ (60 µL; 0.080 mol/L in isopropylalcohol (i-PrOH); 4.6×10$^{-6}$ mol) were combined as in Example 1 and heated for 10 hours at 130° C. After reaction the product mixture was distilled under vacuum to give Silane 2a, N,N[bis(3-(dimethyl(ethoxy)silyl)propyl)-4-aminopyridine, as a colorless liquid (5.75 g; 50%; b.p. 142°-146° C. @ 0.05 torr), which was also characterized by elemental analysis, infrared, $^1$H and

EXAMPLE 4

Synthesis of Silane Monomer 2b:
N,N[Bis(3-(diethoxy(methyl)silyl)propyl)]-4-aminopyridine The title compound was prepared by a the procedure of Example 3 except diethoxy(methyl)silane [(EtO)$_2$MeSiH] was used in the place of the dimethyl(ethoxy)silane. N,N[Bis(3-(diethoxy(methyl)silyl)propyl)]-4-aminopyridine, Silane 2b, was recovered as a colorless liquid (25% yield, b.p. 164°–165° C. @ 0.05 torr), and characterized by elemental analysis, infrared, $^1$H and $^{13}$C-NMR spectroscopy, and gas chromatography-mass spectrometry.

EXAMPLE 5

Synthesis of Silane Monomer 2c:
N,N[Bis(3-(triethoxysilyl)propyl]-4-aminopyridine Silane 2c was prepared by the procedure of Example 3 except triethoxysilane [(EtO)$_3$SiH] was used instead of the dimethyl(ethoxy)silane. N,N[Bis(3-(triethoxysilyl)propyl]-4-aminopyridine, Silane 2c, was recovered as a colorless liquid (20% yield, b.p. 174°–180° C. @ 0.05 torr), and characterized by elemental analysis, infrared, $^1$H and $^{13}$C-NMR spectroscopy, and gas chromatography-mass spectrometry.

EXAMPLE 6

Synthesis of Siloxane 3a: Linear Homopolymer With Pendant DAAP Functions

To a magnetically stirred solution of Silane 1a, N-(3-(diethoxy(methyl)silyl)propyl)-N-methyl-4-aminopyridine, (1.06 g; 0.0028 mol) diluted with THF/i-PrOH (1:1 v/v, 2 mL) was added H$_2$O (99 μL; 0.0055 mol) and Me$_4$NOH (2μL; 20% in MeOH; 4.4×10$^{-6}$ mol). The mixture was stirred for 12 hours at room temperature. Volatile materials were removed by heating to 60° C. for 12 hours under vacuum. The residue was dissolved in CH$_2$Cl$_2$ (5 mL) and hexamethyldisilazane was added. The mixture was stirred at room temperature for 12 hours. Volatile materials were removed under vacuum and the polymeric product was heated under vacuum at 80° C. for 12 hours. The temperature was then raised to 140° C. for 20 minutes. The Siloxane 3a product is a pale-yellow, viscous fluid, with molecular weight dependent on the ratio of monomer-to-catalyst and conditions of reaction. Polymer 3a is soluble in CH$_2$Cl$_2$, THF, and methanol, was characterized by elemental analysis, spectroscopic methods and thermal analysis (DSC and TGA), and exhibited a T$_d$ of 375° C.

EXAMPLE 7

Synthesis of Polymer 5a: Linear Homopolymer With DAAP Functions in Backbone

N,N[Bis(3-(dimethyl(ethoxy)silyl)propyl)]-4-aminopyridine, Silane 2a, (0.85 g; 0.0030 mol) was dissolved in THF/i-PrOH (1:1 v/v, 2 mL). H$_2$O (108 μL; 0.0060 mol) and Me$_4$NOH (2μL; 20% in MeOH; 4.4×10$^{-6}$ mol) were added and the mixture was stirred for 12 hours at room temperature. Volatile materials were removed by heating under vacuum at 60° C. for 12 hours. The resulting viscous fluid was dissolved in CH$_2$Cl$_2$ and hexamethyldisilazane (1 mL) was added. The mixture was stirred for 8 hours, then the volatile materials were removed under vacuum at 80° C. for 12 hours. The temperature was raised to 140° C. for 20 minutes. The pale-yellow, viscous polymeric 5a product has a molecular weight dependent on the ratio of monomer-to-catalyst and conditions of reaction. Siloxane 5a is soluble in CH$_2$Cl$_2$, THF, ether, toluene and methanol, was characterized by elemental analysis, spectroscopic methods and thermal analysis (DSC and TGA), and demonstrated a T$_d$ of 427° C.

EXAMPLE 8

Synthesis of Siloxane 4a: Linear Co-polymer With Pendant DAAP Functions

N-(3-(Diethoxy(methyl)silyl)propyl)-N-methyl-4-aminopyridine (Silane 1a), and cyclic polysiloxane [(Me$_2$SiO)$_3$ or (Me$_2$SiO)$_4$)] or hydroxyl terminated linear oligomer [HO(SiMe$_2$O)$_n$OH, n=less than 10] (>1 equiv), end-blocking agent (Me$_3$Si)$_2$O (<0.01 equiv.), and catalyst (Me$_4$NOH or potassium silanolate), were stirred at 60° C. for 12 hours. The mixture was then heated under vacuum at 140° C. for 6 hours. The resulting co-polymer 4b is a pale yellow viscous fluid which is soluble in organic solvents such as halogenated hydrocarbons, and THF, and has a T$_d$ from 370° C. to 445° C. depending upon the relative quantities of the reactants and molecular weight, and to some extent of course upon the purity of the sample tested. The molecular weight of the co-polymer obtained depended on the ratio of reaction monomer and co-oligomer, and the relative quantities of (Me$_3$Si)$_2$O and catalyst.

EXAMPLE 9

Synthesis of Siloxane 5b: Linear Co-Polymer With DAAP Functions In Backbone

The procedure of Example 8 was repeated except N,N[bis(3-(dimethyl(ethoxy)silyl)propyl)]-4-aminopyridine was used instead of N-(3-(diethoxy(methyl)silyl)propyl)-N-methyl-4-aminopyridine. The resulting co-polymer 5b is a pale yellow viscous fluid which is soluble in halogenated and aromatic hydrocarbons, and THF, and has a T$_d$ of 425° C. to 455° C. depending upon the relative quantities of reactants used in preparation and molecular weight, and of course to some extent upon purity. The molecular weight of the co-polymer obtained depended on the relative quantities of reactants used and the relative quantities of (Me$_3$Si)$_2$O and catalyst.

EXAMPLE 10

Synthesis of Siloxanes 4a and 6a: Crosslinked Co-polymers With DAAP Functions Pendant From or Included in Polymer Backbone In representative experiments, N-(3-(diethoxy(methyl)silyl)propyl)-N-methyl-4-aminopyridine or N,N[bis(3-(dimethyl(ethoxy)silyl)propyl)-4-aminopyridine (Silane 1a or 2a) was dissolved in a mixture of THF and i-PrOH (1:1 v/v). Crosslinking agent [methyltriethoxysilane (0.50 equiv.)], NH$_3$(aq) (3 equiv., 6N), and Me$_4$NOH were added to the solution and the mixture was stirred for 12 hours at 60° C. Volatile materials were removed by heating the mixture at 80° C. for 12 hours under vacuum. The temperature of the residue was raised to 140° C. for 6 hours. The resulting polymer products (4a and 6a, respectively) are rubbery materials which swell in CH$_2$Cl$_2$ or THF, and have respective T$_d$'s of 460° C. and 375° C. Table 1 below summarizes these two experiments and similar experiments using varying crosslinking agent and co-monomer combinations (numbers in parentheses represent equivalents used).

TABLE 1

| Species | Monomer (mol) | Co-reactant (mol) | Crosslink. Agent (mol) | Properties |
|---------|---------------|-------------------|------------------------|------------|
| 4a | 1a (1.0) | (none) | MeSi(OEt)$_3$ (0.50) | rubbery |
| 4b | 1a (1.0) | Me$_2$Si(OEt)$_2$ (1.0) | MeSi(OEt)$_3$ (0.60) + Si(OEt)$_4$ (0.20) | solid resin |
| 4b | 1a (1.0) | (Me$_2$SiO)$_3$ (0.50) | MeSi(OEt)$_3$ (0.50) | solid resin |
| 6a | 2a (1.0) | (none) | MeSi(OEt)$_3$ (0.50) | rubbery |
| 6b | 2a (1.0) | (Me$_2$SiO)$_3$ (0.50) | MeSi(OEt)$_3$ (0.50) | solid resin |

EXAMPLE 11

Polymer from Silane Monomer 2b Crosslinked Homopolymer With DAAP Functions in Backbone A procedure analogous to that of Example 10 (except no crosslinking agent or co-reactant was added) was used to prepare a crosslinked homopolymer from silane 2b, N,N[bis(3-(diethoxy(methyl)silyl)propyl)]-4-aminopyridine. The resulting siloxane polymer is a highly crosslinked resin exhibiting good DAAP catalytic properties as illustrated in Table 2 below.

EXAMPLE 12

Polymer from Silane Monomer 1b

To a magnetically stirred solution of N-(3-(triethoxysilyl)propyl)-N-methyl-4-aminopyridine (silane 1b) (0.50g; 1.6 mmol) diluted with THF/i-PrOH (1 mL, 1:1) in a 25 mL round bottom flask under nitrogen was added NH$_3$ (aq) (90 mL; 6N) and Me$_4$NOH (2 mL; 20% in MeOH; 4.4×10$^{-6}$ mol). The mixture was stirred for 6 hours at room temperature and then heated at 60° C. for 12 hours. Volatile materials were removed by heating at 90° C. for 12 hours under vacuum. The residue is a brown solid which is soluble in organic solvents such as CH$_2$Cl$_2$, CHCl$_3$ and THF. The product was dissolved in CH$_2$Cl$_2$ (5 mL) and excess hexamethyldisilazane was added. This mixture was stirred for 12 hours at ambient temperature, and the resulting polymer was re-precipitated three times from CH$_2$Cl$_2$ solution by addition of hexane. Solvents were decanted and the product was dried under vacuum for 12 hours at 90° C. The temperature was then raised to 140° C. for 20 minutes thus leaving a brown solid which is soluble in organic solvents such as CH$_2$Cl$_2$, CHCl$_3$ and THF and exhibits a T$_d$ of 400° C.

EXAMPLE 13

Catalytic Rate in Transacylation of Sterically Hindered Alcohol and Anhydride

An accepted standard test for the ability of a catalyst to effect a transacylation is the reaction of a sterically hindered alcohol with an anhydride such as acetic anhydride. Thus, the several 4-aminopyridyl reagents listed in Table 2 were compared as described in the following experiment: Acetic anhydride (1 mL; 0.010 mol) was added with stirring to a solution which contained 1-methylcyclohexanol (0.57 g; 0.0050 mol), triethylamine (1 mL; 0.0075 mol), dodecane (0.200 mL; 8.8×10$^{-4}$ mol) and catalyst (1 mmol). The mixture was stirred at room temperature for 17 and 31 hours. Yields of product were determined by gas-liquid chromatography and are set forth in Table 2 below.

TABLE 2

| Catalyst | Time (h) | Product Yield (%) |
|----------|----------|-------------------|
| DMAP[a] | 17 | 98 |
|  | 31 | 100 |
| Poly(diallylaminopyridine)[b] [hereafter Poly(diallylAP)] | 17 | 12 |
|  | 31 | 20 |
| Poly(diallyAP-co-DMAM)[c] | 17 | 28 |
|  | 31 | 42 |
| Siloxane 3a | 17 | 79 |
|  | 31 | 89 |
| Siloxane 5a | 17 | 83 |
|  | 31 | 91 |
| Siloxane 4a | 17 | 67 |
|  | 31 | 76 |
| Siloxane 6a | 17 | 65 |
|  | 31 | 77 |
| Polymer of Example 11 | 17 | 65 |
|  | 31 | 77 |

[a] 4-Dimethylaminopyridine

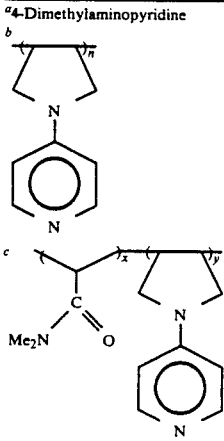

While certain preferred embodiments of the invention have been described in the forgoing description and its specific Examples, the same is to be considered as illustrative and not restrictive in character, it being understood that only the preferred embodiment has been described and that all changes and modifications that come within the spirit of the invention are desired to be protected.

What is claimed is:

1. A nucleophilic and basic composition comprising a silane incorporating 4-dialkylaminopyridine functionality.

2. The composition of claim 1 which comprises a silane including a 4-dialkylaminopyridine group having at least one alkoxysilyl group connected to its 4-dialkylamino moiety.

3. The composition of claim 2 which comprises a silane including a single 4-dialkylaminopyridine group having a single alkoxysilyl group connected to its 4-dialkylamino moiety.

4. The composition of claim 3 wherein the alkoxysilyl group is at least a dialkoxysilyl group.

5. The composition of claim 3 wherein the alkoxysilyl group is a trialkoxysilyl group.

6. The composition of claim 4 wherein the alkoxy groups are methoxy, ethoxy or propoxy groups.

7. The composition of claim 5 wherein the alkoxy groups are methoxy, ethoxy or propoxy groups.

8. N-(3-(Diethoxy(methyl)silyl)propyl)-N-methyl-4-aminopyridine, a composition according to claim 6.

9. N-(3-(Triethoxysilyl)propyl)-N-methyl-4-aminopyridine, a composition according to claim 7.

10. The silane of claim 2 which includes a single 4-dialkylaminopyridine group having two alkoxysilyl groups attached to its 4-dialkylamino moiety.

11. The composition of claim 10 wherein each alkoxysilyl group is at least a dialkoxysilyl group.

12. The composition of claim 10 wherein each alkoxysilyl group is a trialkoxysilyl group.

13. N,N[Bis(3-(dimethyl(ethoxy)silyl)propyl)]-4-aminopyridine, a composition according to claim 10.

14. N,N[Bis(3-(diethoxy(methyl)silyl)propyl)]-4-aminopyridine, a composition according to claim 11.

15. N,N[Bis(3-(triethoxysilyl)propyl)]-4-aminopyridine, a composition according to claim 12.

16. An aminopyridyl silane having the formula:

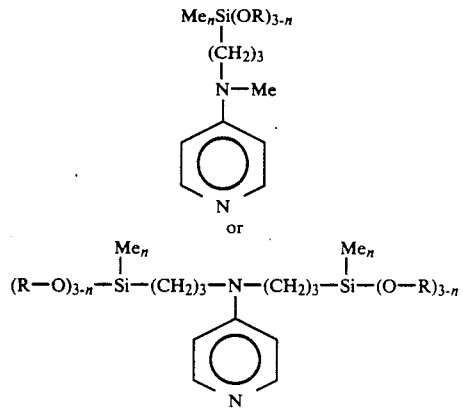

wherein
Me = methyl
$n = 0$, 1 or 2; and
R = lower alkyl.

17. The silane of claim 16 wherein $n=2$.

18. The silane of claim 16 wherein $n=1$.

19. The silane of claim 16 wherein $n=0$.

20. The silane of claim 17, 18 or 19 wherein R = methyl, ethyl, propyl or iso-propyl.

21. The silane of claim 20 wherein R = ethyl.

* * * * *